(12) United States Patent
Shieh et al.

(10) Patent No.: US 8,017,799 B2
(45) Date of Patent: Sep. 13, 2011

(54) HEXAHYDROPHTHALATE BASED COMPOUND AND PROCESS FOR PRODUCING THE SAME

(75) Inventors: Sung-Yueh Shieh, Taipei (TW); Dein-Run Fung, Taipei (TW); Han-Ching Hsu, Taipei (TW); Yang-Tu Liu, Taipei (TW)

(73) Assignee: Nan Ya Plastics Corporation, Taipei (TW)

( * ) Notice: Subject to any disclaimer, the term of this patent is extended or adjusted under 35 U.S.C. 154(b) by 196 days.

(21) Appl. No.: 12/318,551

(22) Filed: Dec. 31, 2008

(65) Prior Publication Data

US 2009/0281349 A1    Nov. 12, 2009

(30) Foreign Application Priority Data

May 6, 2008    (TW) ............................... 97116586 A

(51) Int. Cl.
  *C07C 69/74*    (2006.01)
(52) U.S. Cl. ...................................... 560/127
(58) Field of Classification Search .......... None
  See application file for complete search history.

(56) References Cited

U.S. PATENT DOCUMENTS

2005/0020718 A1 *  1/2005  Gosse et al. .................. 523/105

FOREIGN PATENT DOCUMENTS

JP    62030141 A  *  2/1987

OTHER PUBLICATIONS

Mukhamedova et al, Neftekhimiya, 1963, 3(6), 900-4.*

* cited by examiner

*Primary Examiner* — Sudhakar Katakam
(74) *Attorney, Agent, or Firm* — Bacon & Thomas, PLLC

(57) ABSTRACT

A hexahydrophthalate based compound is adapted to use as a plasticizer that contains no phthalic acid and benzoic acid, possess physical properties superior to DEHA and DINA in transparency and adhesion and is friendly to organisms and the environment; and a process for producing the hexahydrophthalate based compound includes esterifying hexahydrophthalic anhydride, a diol, and a catalyst for decarboxylation to get hexahydrophthalic alcohol, and adding a monoacid into the hexahydrophthalic alcohol for further esterification, thereby obtaining the hexahydrophthalate based compound.

7 Claims, No Drawings

HEXAHYDROPHTHALATE BASED COMPOUND AND PROCESS FOR PRODUCING THE SAME

BACKGROUND OF THE PRESENT INVENTION

1. Field of the Present Invention

The present invention relates to hexahydrophthalate based compound and a process for producing the same. More particularly, the present invention relates to hexahydrophthalate based compound adapted to use as a plasticizer that contains no phthalic acid and benzoic acid, possess physical properties superior to DEHA and DINA in transparency and adhesion and is friendly to organisms and the environment, and a process for producing the same.

2. Description of Prior Art

As known in the art, plasticizers provide capability of being processed, flexibility, and electrical insulation property to resins, such as PVC resin, during finishing thereof. Besides, plasticizers present swelling effect and are dissolvable in resins to form even films. As compared with resins without plasticizers, resins with plasticizers are advantageous to lower thermoplastic temperature, improve flowing and forming ability when heated up, enhance elasticity and reduce hardness.

Presently, the most popular plasticizers are those made of phthalic anhydride, such as Di-2-ethylhexyl phthalate (DOP) and Di-iso-nonyl phthalate (DINP). However, according to researches and reports, such plasticizers can bring environmental hormone-related problems and therefore are ecologically adverse. On the other hand, plasticizers referred to Di(2-ethylhexyl)adipate (DEHA) made of adipic acid are suspected to be harmful to human liver.

As to food packing materials, adhesion and transparency of PVC films are highly required. Food packing materials added with DEHA plasticizers are officially banned for being suspected to be harmful to human health. Food-packing materials added with DINA plasticizers feature improved migration of plasticizers due to increased molecular weight, and yet are flawed by deteriorated adhesion.

In the known prior art, U.S. Pat. No. 3,110,603 discloses polyalkylene glycol dibenzoate highly miscible with PVC resin but inefficient in plasticizing due to benzene rings structurally existing therein. In Publication No. WO2005023926, a diethyleneglycol ester based plasticizer is proposed, wherein the compound is produced from benzoic acid with excessive acidity. However, the compound contains benzene rings and has a relatively low molecular weight, tending to be volatile during a finishing process.

SUMMARY OF THE INVENTION

One objective of the present invention is to provide a hexahydrophthalate based compound without phthalates and benzoic acids that contain benzene rings.

The proposed hexahydrophthalate based compound of the invention is selected from the group consisting of the formula

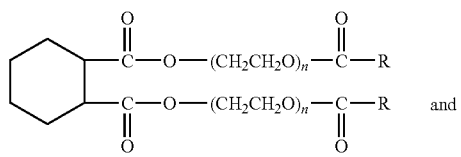

and

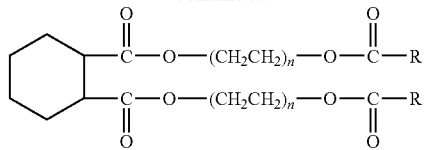

wherein $n=2, 3, 4, 5$ or $6$, and R is alkyl of $C_3$-$C_{11}$.

The proposed hexahydrophthalate based compound is adapted to act as a plasticizer for use in a finishing process of resins, such as polyvinyl chloride (PVC) resin, wherein the plasticizer has improved quality and processing physical property as compared with DEHA plasticizers while being friendly to organisms and the environment.

Another objective of the present invention is to provide a PVC film for food packing using the aforementioned hexahydrophthalate based compound as a plasticizer. Since the hexahydrophthalate based compound structurally contains relatively higher concentration of ester groups and ether groups, it is highly miscible with PVC resin to contribute desired adhesion to the PVC packing film while being environment-friendly for containing no benzene ring therein.

Further objective of the present invention is to provide a process for producing the hexahydrophthalate based compound, comprising steps of:

(a) providing $C_4$-$C_{12}$ diol and hexahydrophthalic anhydride as materials of a reactant, placing the reactant into a reactor in presence of a catalyst for esterification, introducing gaseous $N_2$ into the reactor before performing esterification, and performing esterification at 150° C.-260° C. for 3-10 hours until an acidity of the reactant becomes less than 3.0 mgKOH/g to obtain hexahydrophthalic alcohol; wherein the $C_4$-$C_{12}$ diol is one of $C_4$-$C_{12}$ straight-chain diols, $C_4$-$C_{12}$ side-chain diols, $C_4$-$C_{12}$ diol compounds having ether groups, PEG-200 and PEG-400;

(b) adding $C_4$-$C_{12}$ monoacid into the reactor for further esterification with the hexahydrophthalic alcohol obtained in the Step (a), wherein a molar ratio of the monoacid to the hexahydrophthalic alcohol is 99.5:100-80:100, introducing gaseous $N_2$ into the reactor before performing esterification, and performing esterification at 150° C.-260° C. for 3-10 hours until the acidity of the reactant becomes less than 5.0 mgKOH/g to finalize esterification; and (c) neutralizing the reactant obtained in the Step (b) with an aqueous alkali metal hydroxide solution, and then distilling, dehydrating, drying, filtering and purifying the neutralized reactant successively to obtain the hexahydrophthalate based compound with desired color and purity.

DETAILED DESCRIPTION OF THE PREFERRED EMBODIMENT

The present invention proposes a hexahydrophthalate based compound without phthalates and benzoic acids that contain benzene rings. The proposed hexahydrophthalate based compound of the invention is selected from the group consisting of the formula

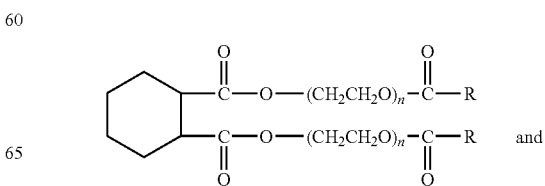

and

-continued

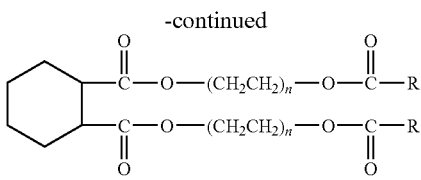

wherein n=2, 3, 4, 5 or 6, and R is alkyl of $C_3$-$C_{11}$.

The proposed hexahydrophthalate based compound is configured to act as a plasticizer for use in a finishing process of resins, such as polyvinyl chloride (PVC) resin.

A process for producing hexahydrophthalate based compound comprises a first-stage esterification, a second-stage esterification, a neutralization and rinsing, a distillation, a dehydration and a filtration, which will be described in detail below.

First-Stage Esterification:

To optimize the plasticizing effect of a product, during the first-stage esterification, $C_4$-$C_{12}$ diol and hexahydrophthalic anhydride are received in a reactor equipped with stir bars and a condenser in presence of a catalyst for esterification. Therein, the diol is overproduced by 0.1%-20% in mole. The catalyst accounts for 0.1 wt %-3.0 wt % of the total weight of the reactant and may be, but not limited to, an acid, such as toluene sulfonic acid, or an organic metal, such as tetraisopropyl titanate. An azeotrope solvent, such as xylene, is added. The azeotrope solvent accounts for 1.0 wt %-15.0 wt % of the total weight of the reactant.

Gaseous $N_2$ is introduced into the reactor before esterification, and then esterification is performed at 150° C.-260° C. for 3-10 hours until the acidity of the reactant becomes less than 3.0 mgKOH/g. The reaction yields hexahydrophthalic alcohol before proceeding to the second-stage esterification.

Second-Stage Esterification:

$C_4$-$C_{12}$ monoacid is added into the reactor for the second-stage esterification. The molar ratio of the monoacid to the hexahydrophthalic alcohol is 99.5:100-80:100. Gaseous $N_2$ is introduced into the reactor before esterification, and then esterification is performed at 150° C.-260° C. for 3-10 hours until the acidity of the reactant becomes less than 5.0 mgKOH/g so as to finalize esterification.

Neutralization and Rinsing:

After the two stages of esterification, the reactant is treated by neutralization and rinsing processes. An aqueous alkali metal hydroxide solution is prepared as a neutralization agent for reacting with residual acid left behind after esterification to form salts. The concentration of alkali metal hydroxide in the solution is 3-20 wt %, preferably 5-15 wt %. After neutralization, the reactant is well rinsed to remove the salts generated as products of the neutralization.

Distillation:

After rinsing, the reactant is distilled to remove the aqueous solution to obtain anhydrous particles of the reactant.

Dehydration and Filtration:

The dehydration may, or may not, involve introducing an inert gas, as long as redundant water can be removed from the reactant. The dehydrated reactant is then filtered for removal of impurities to obtain the hexahydrophthalate based compound with desired color and purity.

The filtration may be conducted at room temperature or higher temperature and may use any known filter, such as cellulose, kieselguhr or wood flour.

When used as a plasticizer for PVC resin finishing, the disclosed hexahydrophthalate based compound possesses the quality and processing physical properties equivalent to those of normal phthalic acid-based plasticizers, such as DOP and DINP, and DEHA plasticizers and DINA plasticizers. Thus, the plasticizer of the disclosed hexahydrophthalate based compound can be widely used in manufacturing of a variety of plastic products, such as stationery, food packing materials, toys, appliances for children, waterbeds, inflatable products, food containers, baby carriages, bottle caps, household gloves, medical articles, packing for cosmetics, and so on.

While some embodiments and comparative embodiments will be given below for illustrating the effects of the present invention, it is to be understood that the scope of the present invention is not limited to the recited embodiments.

Method for Measuring Physical Properties of PVC Film

Transparency Test

Ten pieces of PVC film each being 0.4 mm thick, 2.5 cm wide, and 5 cm long are piled up and pressed in a pressing machine at 165° C. for 3.5 minutes to obtain a PVC lamination 3 mm thick. After being cooled, the PVC film is measured for transparency thereof.

Hardness Test

Three pieces of PVC film each being 0.4 mm thick are stacked and pressed into a PVC lamination 1.0 mm thick. Then, the PVC lamination is divided into segments each being 1.0 mm thick, 2.0 cm wide, and 3.0 cm long.

Six said segments are packed and stacked up to 6 mm in thickness and laid rested at 23° C. for 24 hours. Afterward, the stacked segments are measured at five different positions thereon by a hardness measurement device whose readings are taken after 15 seconds from the beginning of each measurement. Three of the readings are used to determine an average hardness of the stacked segments.

Adhesion Test

Two pieces of PVC film each being 0.1 mm thick, 3.0 cm wide, and 30 cm long are stacked up and then compressed to expel air that may otherwise exist therebetween. Then, adhesion between the two pieces of PVC film is measured.

Embodiment 1

Hexahydrophthalic anhydride of 0.5 mole, diethylene glycol of 1.15 moles, catalyst TIPT (Tetraisopropyl titanate) of 1.0 g and xylene of 34.0 g are received in a four-neck flask equipped with magnetic stir bars and a condenser for reaction at 160° C.-180° C. for 5 hours while the reactant is dehydrated during esterification. Esterification lasts until the acidity of the reactant becomes less than 3 mgKOH/g. Afterward, 0.96 mole of 2-EHA is added and esterification continues at 160° C.-230° C. for 5 hours until the acidity of the reactant becomes less than 5 mgKOH/g to finalize esterification.

After esterification, the reactant is treated by an aqueous alkali metal hydroxide solution, and then rinsed by water, distilled, dehydrated, and filtered to obtain the hexahydrophthalate based compound with desired color.

The obtained hexahydrophthalate based compound is used as a plasticizer for a finishing process of PVC resin. Two shares of powder samples are prepared, each containing polyvinyl chloride resin (available from Formosa Petrochemical Co., Taiwan, S-65 branded) of 100 g, the hexahydrophthalate based compound of 40 g, and barium-zinc stabilizer (available from Nan Ya plastics Corporation, Taiwan, LQX19T) of 2 g. Both samples are respectively mixed by a roller at 170□ for 5 minutes to form PVC films having thickness of 0.4 mm and thickness of 0.1 mm, respectively.

The transparency and hardness of the PVC film having thickness of 0.4 mm are measured. The adhesion of the PVC film having thickness of 0.1 mm is measured. The measured results are shown in Table 1.

Embodiment 2

Hexahydrophthalic anhydride of 0.5 mole, triethylene glycol of 1.05 moles, catalyst TIPT (Tetraisopropyl titanate) of 1.0 g and xylene of 34.0 g are received in a four-neck flask equipped with magnetic stir bars and a condenser for reaction at 160° C.-180° C. for 5 hours while the reactant is dehydrated during esterification. Esterification lasts until the acidity of the reactant becomes less than 3 mgKOH/g. Afterward, 0.97 mole of 2-EHA is added and esterification continues at 160° C.-230° C. for 5 hours until the acidity of the reactant becomes less than 5 mgKOH/g to finalize esterification.

After esterification, the reactant is treated by an aqueous alkali metal hydroxide solution, and then rinsed by water, distilled, dehydrated, and filtered to obtain the hexahydrophthalate based compound with desired color.

The obtained hexahydrophthalate based compound is used as a plasticizer for a finishing process of PVC resin. Two PVC films having thickness of 0.4 mm and thickness of 0.1 mm, respectively, are formed as described in Embodiment 1.

The transparency and hardness of the PVC film having thickness of 0.4 mm are measured. The adhesion of the PVC film having thickness of 0.1 mm is measured. The measured results are shown in Table 1.

Embodiment 3

Hexahydrophthalic anhydride of 0.5 mole, PEG-200 of 1.03 moles, catalyst TIPT (tetraisopropyl titanate) of 1.0 g and xylene of 34.0 g are received by a four-neck flask equipped with magnetic stir bars and a condenser to undergo reaction at 160° C.-180° C. for 5 hours while the reactant is dehydrated during esterification. Esterification lasts until the acidity of the reactant becomes less than 3 mgKOH/g. Afterward, 0.95 mole of 2-EHA is added and esterification continues at 160° C.-230° C. for 5 hours until the acidity of the reactant becomes less than 5 mgKOH/g to finalize esterification.

After esterification, the reactant is treated by an aqueous alkali metal hydroxide solution, and then rinsed by water, distilled, dehydrated, and filtered to obtain the hexahydrophthalate based compound with desired color.

The obtained hexahydrophthalate based compound is used as a plasticizer for a finishing process of PVC resin. Two PVC films having thickness of 0.4 mm and thickness of 0.1 mm, respectively, are formed as described in Embodiment 1.

The transparency and hardness of the PVC film having thickness of 0.4 mm are measured. The adhesion of the PVC film having thickness of 0.1 mm is measured. The measured results are shown in Table 1.

Comparative Embodiment 1

Di(2-ethylhexyl)adipate (DEHA) is used as a plasticizer for finishing PVC resin. Two PVC films having thickness of 0.4 mm and thickness of 0.1 mm, respectively, are formed in the manner as described in Embodiment 1.

The transparency and hardness of the PVC film having thickness of 0.4 mm are measured. The adhesion of the PVC film having thickness of 0.1 mm is measured. The measured results are shown in Table 1.

Comparative Embodiment 2

Di-isononyl adipate (DINA) is used as a plasticizer for finishing PVC resin. Two PVC films having thickness of 0.4 mm and thickness of 0.1 mm, respectively, are formed in the manner as described in Embodiment 1.

The transparency and hardness of the PVC film having thickness of 0.4 mm are measured. The adhesion of the PVC film having thickness of 0.1 mm is measured. The measured results are shown in Table 1.

TABLE 1

|  | Transparency | Hardness | Adhesion |
| --- | --- | --- | --- |
| Embodiment 1 | excellent | good | outstanding |
| Embodiment 2 | excellent | good | outstanding |
| Embodiment 3 | excellent | good | good |
| Comparative Embodiment 1 | good | good | good |
| Comparative Embodiment 2 | good | good | acceptable |

Results

From the Table 1, the results of the measurements indicate that the hexahydrophthalate based compounds obtained from Embodiments 1-3 possess physical properties superior to DEHA and DINA in transparency and adhesion and also equivalent to DEHA or DINA plasticizers in hardness (plasticizing effect).

What is claimed is:

1. A hexahydrophthalate based compound, adapted to use as a plasticizer for finishing PVC resin, is selected from the group consisting of the formula

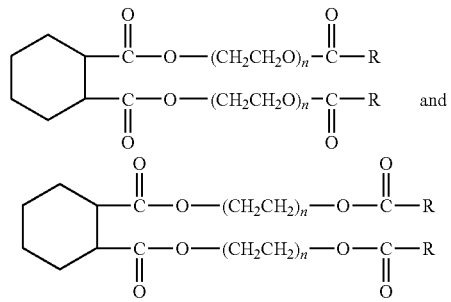

wherein n=4, 5 or 6, and R is alkyl of $C_3$-$C_{11}$.

2. A process for producing hexahydrophthalate based compound selected from the group consisting of the formula

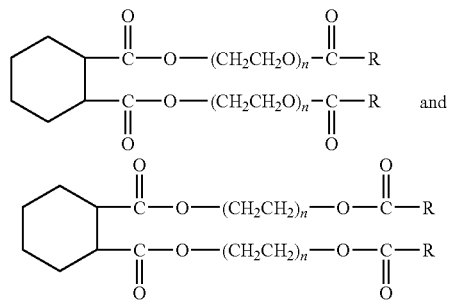

wherein n=4, 5 or 6, and R is alkyl of $C_3$-$C_{11}$,
comprising the steps of:
(a) providing $C_4$-$C_{12}$ diol and hexahydrophthalic anhydride as materials of a reactant, placing the reactant into a reactor in presence of a catalyst for esterification, introducing gaseous $N_2$ into the reactor before performing esterification, and performing esterification at 150° C.-260° C. for 3-10 hours until an acidity of the reactant becomes less than 3.0 mgKOH/g to obtain hexahydrophthalic alcohol;

(b) adding $C_4$-$C_{12}$ monoacid into the reactor for further esterification with the hexahydrophthalic alcohol obtained in the Step (a), wherein a molar ratio of the monoacid to the hexahydrophthalic alcohol is 99.5:100-80:100, introducing gaseous $N_2$ into the reactor before performing esterification, and performing esterification at 150° C.-260° C. for 3-10 hours until the acidity of the reactant becomes less than 5.0 mgKOH/g to finalize esterification; and (c) neutralizing the reactant obtained in the Step (b) with an aqueous alkali metal hydroxide solution, and then distilling, dehydrating, drying, filtering and purifying the neutralized reactant successively to obtain the hexahydrophthalate based compound with desired color and purity.

3. The process for producing hexahydrophthalate based compound as defined in claim 2, wherein the $C_4$-$C_{12}$ diol is one of $C_4$-$C_{12}$ straight-chain dials, $C_4$-$C_{12}$ side-chain diols, $C_4$-$C_{12}$ diol compounds having ether groups, PEG-200 or PEF-400.

4. A plasticizer made of the hexahydrophthalate based compound as defined in claim 1 and configured for use in finishing PVC resin.

5. A hexahydrophthalate based compound as claimed in claim 1, wherein, n is 4.

6. A hexahydrophthalate based compound as claimed in claim 1, wherein, n is 5.

7. A hexahydrophthalate based compound as claimed in claim 1, wherein, n is 6.

* * * * *